(12) United States Patent
Abels et al.

(10) Patent No.: US 7,247,019 B2
(45) Date of Patent: Jul. 24, 2007

(54) ORTHODONTIC BRACKETS MADE FROM POLYMERIC MATERIALS THAT IMPART DESIRED STRENGTH PROPERTIES

(76) Inventors: Norbert Abels, Alleestrasse 30a, 66424 Homburg (DE); Claus-H. Backes, St. Wendeler Strasse 45, 66113 Saarbrücken (DE)

( * ) Notice: Subject to any disclaimer, the term of this patent is extended or adjusted under 35 U.S.C. 154(b) by 137 days.

(21) Appl. No.: 10/835,959

(22) Filed: Apr. 30, 2004

(65) Prior Publication Data

US 2005/0244772 A1 Nov. 3, 2005

(51) Int. Cl.
*A61C 3/00* (2006.01)
(52) U.S. Cl. .................. 433/10; 433/8; 433/11
(58) Field of Classification Search .............. 433/8–16
See application file for complete search history.

(56) References Cited

U.S. PATENT DOCUMENTS

| | | | | |
|---|---|---|---|---|
| 3,750,288 | A | 8/1973 | Culbreth | 32/14 |
| 4,249,897 | A | 2/1981 | Anderson | 433/8 |
| 4,712,999 | A | 12/1987 | Rosenberg | 433/8 |
| 4,976,614 | A | 12/1990 | Tepper | 433/18 |
| 4,983,334 | A | 1/1991 | Adell | 264/16 |
| 5,176,951 | A | 1/1993 | Rudo | 428/229 |
| 5,230,619 | A | 7/1993 | Wong | 433/9 |
| 5,679,299 | A * | 10/1997 | Gilbert et al. | 264/103 |
| 5,707,231 | A | 1/1998 | Watt et al. | 433/8 |
| 5,857,849 | A * | 1/1999 | Kurz | 433/10 |
| 6,120,288 | A | 9/2000 | Deslauriers | 433/9 |
| 6,247,923 | B1 * | 6/2001 | Vashi | 433/10 |
| 6,309,214 | B2 | 10/2001 | Birkel | 433/15 |
| 6,358,043 | B1 | 3/2002 | Mottate et al. | 433/8 |
| 6,655,957 | B2 | 12/2003 | Abels et al. | 433/10 |
| 6,663,385 | B2 | 12/2003 | Tepper | 433/11 |
| 6,843,651 | B2 | 1/2005 | Orikasa | 433/13 |
| 2002/0110778 | A1 | 8/2002 | Abels et al. | 433/11 |
| 2003/0049582 | A1 | 3/2003 | Abels et al. | 433/11 |
| 2003/0073051 | A1 | 4/2003 | Kyritsis | 433/8 |
| 2003/0190577 | A1 | 10/2003 | Shin et al. | 433/9 |
| 2004/0013994 | A1 * | 1/2004 | Goldberg et al. | 433/8 |
| 2004/0072117 | A1 | 4/2004 | Farzin-Nia et al. | 433/10 |

OTHER PUBLICATIONS

Örtendahl, Thomas, "The Esthetic Biological Concept" course outline (Dec. 2003).
Degussa AG, "Trogamid®, Transparent Polyamides With An Outstanding Combination of Properties" Trogamid T Grades (Dec. 2003).
Degussa AG, "Trogamid®, Transparent Polyamides With An Outstanding Combination of Properties" Trogamid Handling and Processing (Dec. 2003).

* cited by examiner

*Primary Examiner*—Cris Rodriguez
*Assistant Examiner*—Candice C. Stokes
(74) *Attorney, Agent, or Firm*—Workman Nydegger

(57) ABSTRACT

Orthodontic brackets are manufactured from at least one type of crystalline polymer that enhances the physical properties of the brackets. In one aspect, orthodontic brackets according to the invention may comprise at least one type of polyaryletherketone or crystalline polyamide. Fibers, fillers, flow additives and other components may be added as desired. One or more amorphous polymers may be blended with the crystalline polymer. Crystalline polymers are especially well-suited for the manufacture of self-ligating orthodontic brackets that include a bracket base and ligation cover so as to provide sufficient strength for the bracket base and ligation cover while also providing sufficient flexibility for the hinge element to bend or flex.

22 Claims, 6 Drawing Sheets

ORTHODONTIC BRACKETS MADE FROM POLYMERIC MATERIALS THAT IMPART DESIRED STRENGTH PROPERTIES

BACKGROUND OF THE INVENTION

1. The Field of the Invention

The present invention relates to orthodontic brackets, and more particularly to orthodontic brackets made from specific polymeric compositions that comprise at least one type of crystalline polymer.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct underbites or overbites. For example, orthodontic treatment can improve the patient's occlusion, or enhanced spatial matching of corresponding teeth.

The most common form of orthodontic treatment involves the use of orthodontic brackets and wires, which together are commonly referred to as "braces". Orthodontic brackets, more particularly the orthodontic bases, are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment. End sections of the arch wire are typically captured within tiny appliances known as "buccal tubes" affixed to the patient's molars.

Customarily, an arch wire is held within the arch wire slot by ligatures. More recently, self-ligating brackets have been developed that eliminate the need for separate ligatures. Self-ligating brackets may include a cover associated with the bracket base that closes over and secures the arch wire within the arch wire slot. Examples of self-ligating brackets are disclosed in U.S. Pat. Nos. 3,748,740, 4,077,126, 5,857,849, and 6,071,118.

Conventional brackets requiring ligatures and self-ligating brackets have been formed from a wide variety of materials, including metal, plastic, or a combination thereof. Often brackets made from plastic are fragile and easily damaged, partly because of bracket design, but also because of choice of materials. Because of these difficulties, there is a continuing need for more robust designs, but particularly there is a need for materials from which a bracket may be manufactured to increase strength and durability, while maintaining sufficient flexibility where flexibility is needed.

BRIEF SUMMARY OF THE INVENTION

The present invention is directed to self-ligating orthodontic brackets formed from at least one type of crystalline polymer. The self-ligating orthodontic brackets of the present invention may be of any design, several of which will be disclosed in detail herein. The use of crystalline polymers in forming the orthodontic brackets results in brackets exhibiting increased durability and strength. Amorphous polymeric materials may be blended with the crystalline polymers to provide enhanced elasticity, flexibility, and toughness.

Generally, a self-ligating bracket includes a bracket base, at least one slot for receiving an arch wire disposed on or within the bracket base, and a ligation cover. It is further preferable to incorporate the present invention in a self-ligating orthodontic bracket design that may be formed as a single piece, e.g., wherein the ligation cover is hingedly attached to the bracket base by a flexible hinge element, which reduces manufacturing cost and eliminates any required assembly. Additional features may be included as desired, such as a spring element for urging the ligation cover to remain open in a non-ligating position and/or to remain closed in a ligating position. The brackets may be formed by injection molding or other suitable processes.

The crystalline polymer provides the bracket with increased strength and durability. Strength and durability aid the bracket base in holding the arch wire in place during an orthodontic treatment while reducing or eliminating unwanted deformation (i.e., creep) of the bracket base surrounding the arch wire slot as a result of the mechanical forces transmitted from the arch wire to the bracket base.

An optional amorphous polymeric component is sometimes useful in providing the bracket with enhanced elasticity, flexibility, and toughness. Elasticity, flexibility and toughness aid the ability of hinges and springs to be more easily mechanically deformed without becoming fatigued or broken.

Examples of suitable crystalline polymeric materials are polyaryletherketones and crystalline polyamides, an example of which is trogamid nylon. Examples of suitable optional amorphous polymeric materials are polyetherimides. Other components, such as fillers, flow additives, fibers or other adjuvents known in the art may be added as desired.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The present invention relates to orthodontic brackets comprising at least one crystalline polymeric material. The use of crystalline polymers in forming the orthodontic brackets results in brackets exhibiting increased strength and durability. Amorphous polymeric materials may be added to provide enhanced elasticity, flexibility, and toughness.

One example of a class of suitable crystalline polymers for use in forming orthodontic brackets are polyaryletherketones, a specific example of which is PEEK, manufactured by Victrex USA, Inc., located in Greenville, S.C. The basic unit of the polyaryletherketone sold under the trade name PEEK is as follows:

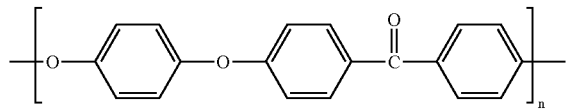

PEEK 151G is a specific grade of PEEK crystalline polymer that is especially useful in forming self-ligating orthodontic brackets according to the invention. PEEK is a thermoplastic polyaryletherketone polymer that is capable of forming a crystalline structure that offers an outstanding combination of physical properties including excellent wear resistance, strength and stiffness.

Crystalline nylons (a type of polyamide) are another class of suitable crystalline polymers for use in forming orthodontic brackets. A specific example of a crystalline nylon is TROGAMID, manufactured by Degussa AG, located in Germany. The basic unit of one type of TROGAMID nylon sold under the trade name TROGAMID T is as follows:

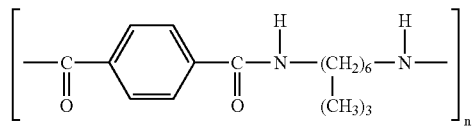

TROGAMID T grade is a specific grade of TROGAMID that is especially useful in forming self-ligating orthodontic brackets according to the invention crystalline polymer. TROGAMID is a thermoplastic polyamide polymer that is capable of forming a crystalline structure that offers an outstanding combination of physical properties including excellent wear resistance, strength and stiffness, and transparency.

According to one embodiment, in addition to at least one type of crystalline polymer, the orthodontic bracket may include an amorphous polymer. Examples of suitable amorphous polymeric materials include polyetherimides, a specific example of which is ULTEM, manufactured by General Electric. ULTEM 1000 and ULTEM 1010 are specific grades of ULTEM that have been found to be useful. ULTEM polymers are amorphous and offer enhanced elasticity, flexibility, and toughness at room temperature. Other suitable materials that could be used as an optional amorphous component include polycarbonate resins, amorphous polyaryletherketone resins, acetal polymer resins, or other amorphous polymer resins known in the art.

Other components, such as fillers, flow additives, glass fibers, carbon fibers, ceramic fibers, or other reinforcing materials known in the art may be added, as desired.

Figure 1:
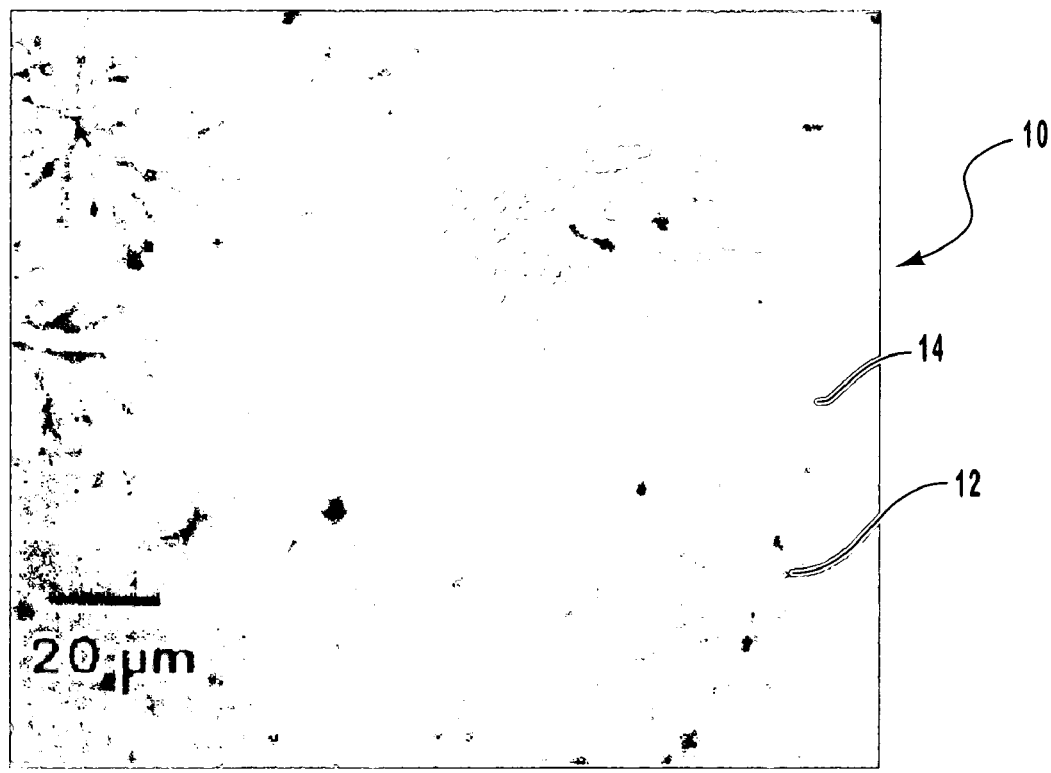
FIG. 1 is a photo micrograph depicting the structure of an exemplary polymer blend comprising a crystalline polymer that may be used to manufacture orthodontic brackets according to the invention.

FIG. 1 is a photo micrograph that depicts a polymeric blend 10 comprising a discrete crystalline phase 12 interspersed together with a discrete amorphous phase 14. The crystalline blend 10 depicted in FIG. 1 comprises PEEK 151G as the crystalline phase 12 and ULTEM 1010 as the amorphous phase 14. In FIG. 1, the crystalline phase 12 generally comprises a disperse phase while the amorphous phase 14 generally comprises a continuous phase into which the disperse crystalline phase is dispersed. Of course in an embodiment where the orthodontic bracket comprises a crystalline polymer and no amorphous polymer, the crystalline phase would be continuous. In addition, with small amounts of amorphous polymer phase, the crystalline phase may also be continuous while the amorphous phase is dispersed.

Self-ligating orthodontic brackets of any desired design may comprise at least one type of crystalline polymer. Generally a self-ligating bracket includes a bracket base, at least one arch wire slot formed within the bracket base, and a ligation cover. The ligation cover is selectively movable between an open and closed position relative to the arch wire slot. The cover may be attached to the base or separate from the base.

The following examples are to be considered in all respects only as illustrative and not restrictive. They are intended to give a general understanding of some applications of the present invention.

Figure 2A:
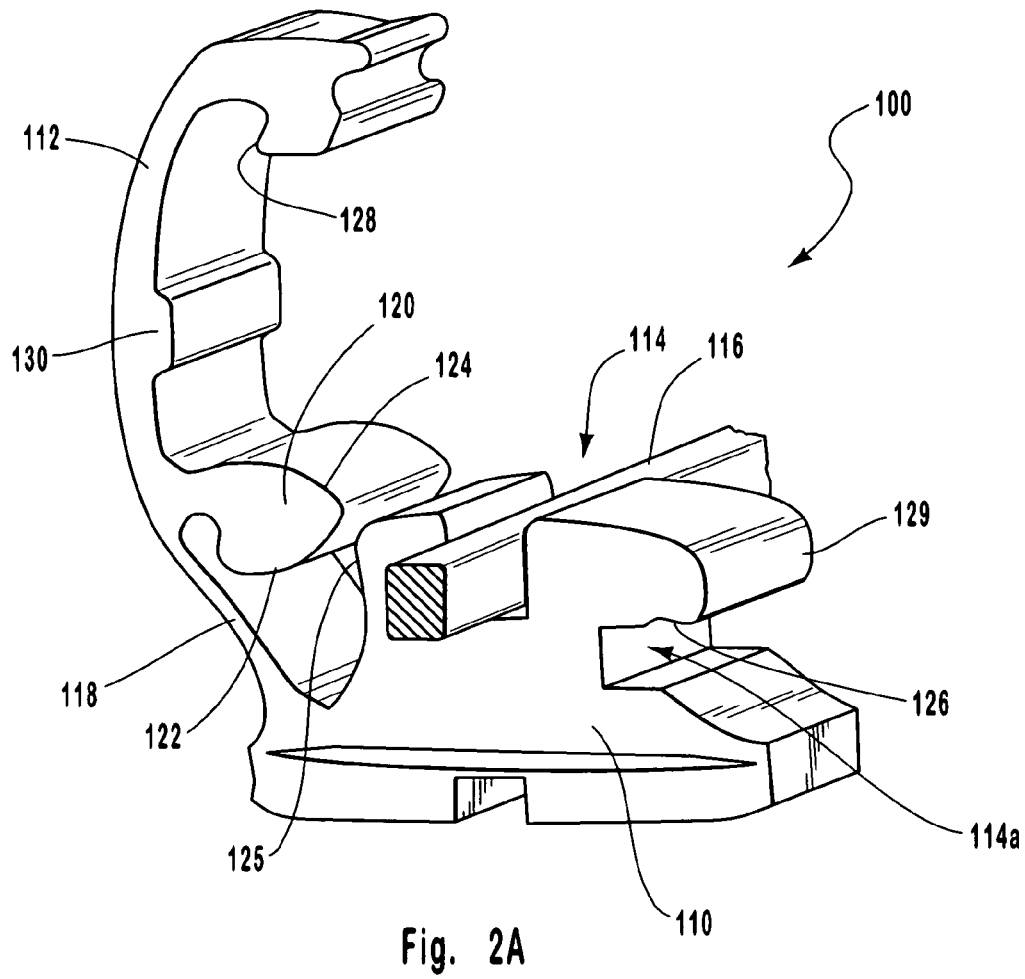
FIGS. 2A-2B illustrate exemplary self-ligating orthodontic brackets that may comprise a crystalline polymer according to the invention.
Figure 2B:
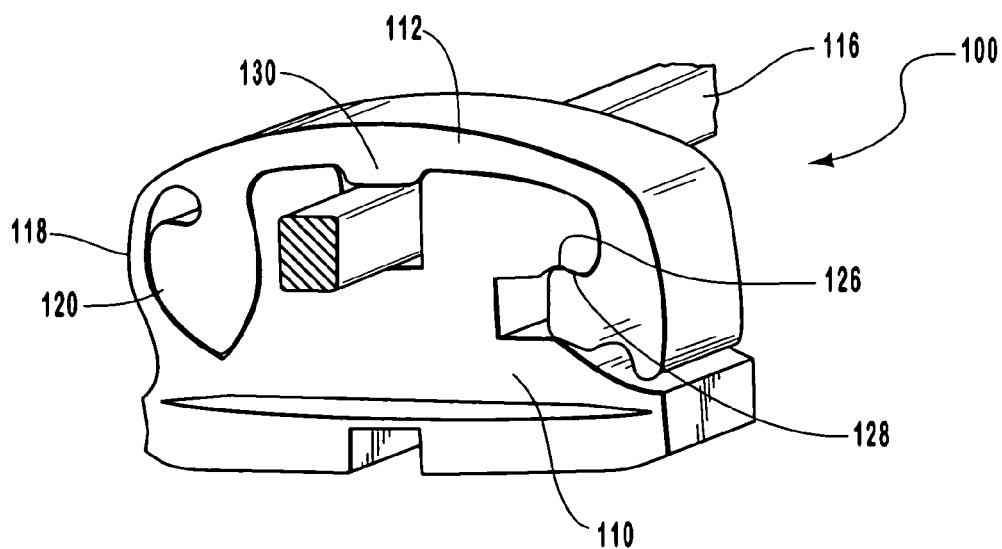

The orthodontic bracket shown in FIGS. 2A-2B may be manufactured in one single piece as an injection molded plastic part from the specific polymeric materials or blends described herein. The orthodontic bracket 100 has a bracket base 110 to which a ligation cover 112 is hingedly attached. A slot 114 open to the upper side of the bracket base 110 is provided near the center of said base 110 and serves for the insertion of an arch wire 116 therein. An additional arch wire slot 114a may also be provided. When forming the bracket from a crystalline polymer, the crystalline polymer lends increased strength, rigidity and durability to the bracket, which is especially important in the region of the base around the slot(s) 114, 114a. Strength, rigidity and durability around the slots 114, 114a prevents or substantially inhibits deformation that may otherwise result because of the mechanical forces transmitted to the base from the arch wire as the teeth are urged into proper alignment. The arch wire 116, shown with a square cross-section (any other cross section known in the art could be used), is arranged inside the slot 114 and serves to correct tooth alignment in a known manner.

The ligation cover 112 is hingedly connected to the bracket base 110 by an elongated film hinge 118. The ligation cover 112 is such that it may be selectively rotated between an open and a closed position relative to the arch wire slot 114, with the ligation cover 112 maintaining the arch wire 116 within the slot 114 when the ligation cover 112 is in the closed, ligating position. The elongated film hinge 118 preferably has a length and thickness that are selected so that the hinge 118 has a desired level of strength, elasticity, flexibility and toughness. In one embodiment, the elongated film hinge 118 has a thickness of at least about 0.2 mm.

The film hinge 118 of this embodiment is designed to bend along substantially its entire length rather than at a single point or line. This helps the hinge resist fatigue or fracture better than film hinges that bend along a single line. In embodiments which include an amorphous polymer, the amorphous component of the blend provides enhanced elasticity, flexibility, and toughness, especially important in the area of the elongated film hinge 118. Elasticity, flexibility, and toughness help the hinge 118 to not become fatigued or broken after repeated bending.

The bracket embodiment illustrated in FIGS. 2A and 2B preferably includes an interactive cam structure 120 with a first curved surface 122 and a second curved surface 124. The first curved surface 122 interacts with the elongated film hinge 118 to provide a curved surface that helps ensure that the elongated film hinge 118 bends gradually over its entire length rather than abruptly at any specific locale. The second curved surface 122 is curved in such a way so that it interacts with a corresponding wall 125 of the base 110 so to bias the ligation cover 112 toward an open position relative to the bracket base 110 when the ligation cover 112 is in the open position. This improves access to arch wire slot 114, making insertion or removal of the arch wire 116 easier. The second curved surface 124 may, depending on the shape of the corresponding wall 125 of the bracket base 110, also act to bias the ligation cover 112 to remain in a closed position when in the closed position relative to the bracket base 110.

An angled keyway 126 is provided near one end of the base 110. The cover 112 contains a corresponding locking tongue 128 that enables the ligation cover 112 to be selectively locked or unlocked relative to the bracket base 110. The ligation cover 112 is locked to bracket base 110 (as seen in FIG. 2B) by closing the cover 112 so that the locking tongue 128 is inserted into angled keyway 126.

In the event that the arch wire 116 pushes against the cover 112 with sufficient force to cause the cover to bulge upwardly relative to the bracket base 110, rather than causing the tongue 128 to withdraw from the angled keyway 126, which could result in undesired disengagement of the cover 112, the locking tongue 128 is instead pulled more deeply into the angled keyway 126, thereby tightening the locking mechanism. This provides added safety, and in order to open the cover, the locking tongue 128 is pulled out of angled keyway 126 and over an outer protrusion 129 of the bracket base 110.

Furthermore, a bearing protrusion 130 is provided at the inside and middle of the cover 112 to assist in fixing the arch wire 116 in the slot 114 while the cover 112 is in the closed state (FIG. 2B). The bearing protrusion 130 reduces the play in the system by effectively widening the ligation cover 112 in the vicinity of the arch wire slot 114.

Figure 3A:
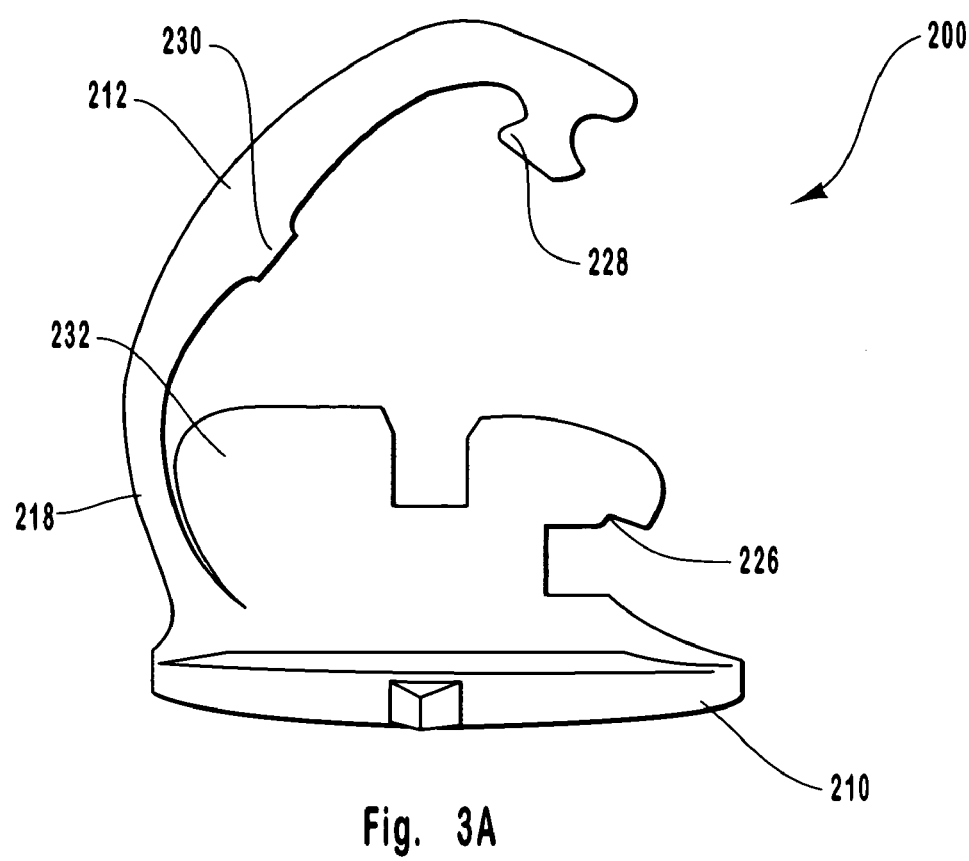
FIGS. 3A-3B illustrate an exemplary self-ligating orthodontic bracket that may comprise a crystalline polymer according to the invention.
Figure 3B:
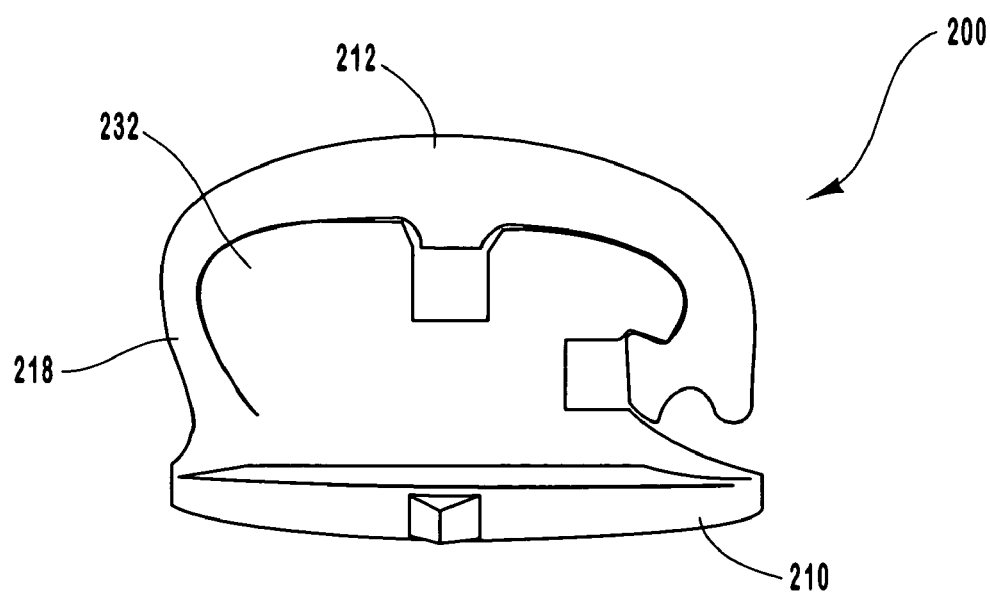

FIGS. 3A and 3B depict an alternative embodiment of an orthodontic bracket 200 according to the invention that does not include a cam structure. Instead, the orthodontic bracket 200 depicted in FIGS. 3A and 3B includes a bracket base 210 and a ligation cover 212 attached to the bracket base 210 by means of an elongate film hinge 218, an angled keyway 226, a locking tongue 228, and a bearing protrusion 230. The bracket base 210 further includes a curved end 232 that acts as a hinge guide in order to cause the elongate film hinge 218 to bend gradually over a significant portion of its entire length. In this way, the curved end 232 of the bracket base 210 acts in similar manner to the curved hinge-guiding surface 122 of the cam structure 120 of the orthodontic bracket 100 depicted in FIGS. 2A-2B. Thus, as the ligation cover 212 is moved from an open, non-ligating position (FIG. 3A) to a closed, ligating position (FIG. 3B), the elongate film hinge 218 at least partially abuts the curved end 232. The abutment between the elongate film hinge 218 and the curved end 232 causes the elongate film hinge 218 to bend gradually around the curved end 232 so as to better distribute the bending forces and bending angles along substantially the entire length of the elongate film hinge 218.

Figure 4A:
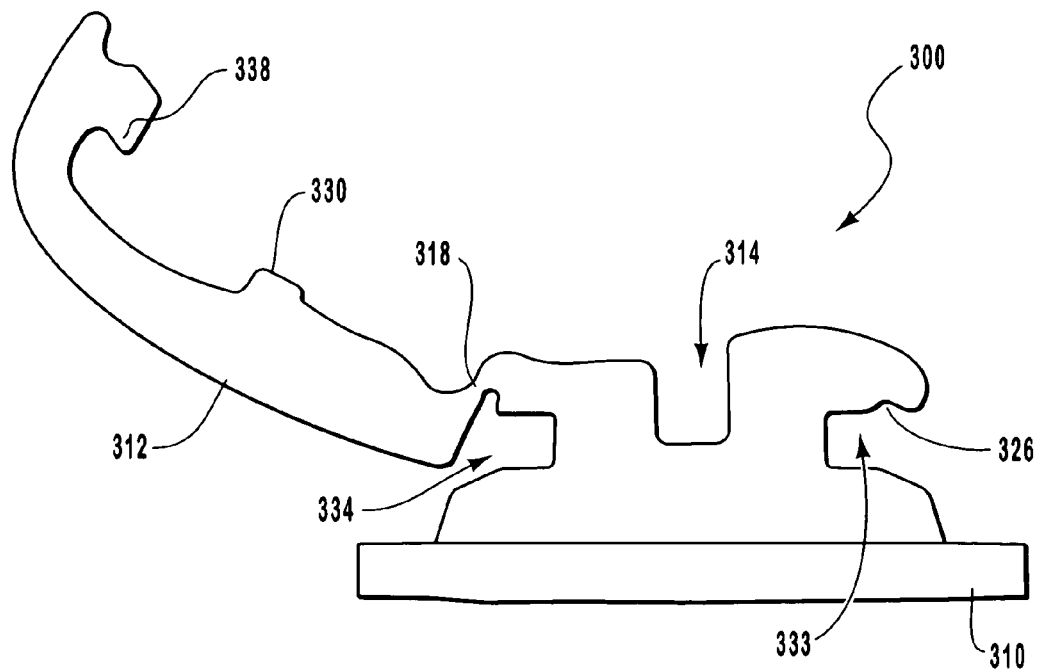
FIGS. 4A-4B illustrate an exemplary self-ligating orthodontic bracket that may comprise a crystalline polymer according to the invention.
Figure 4B:
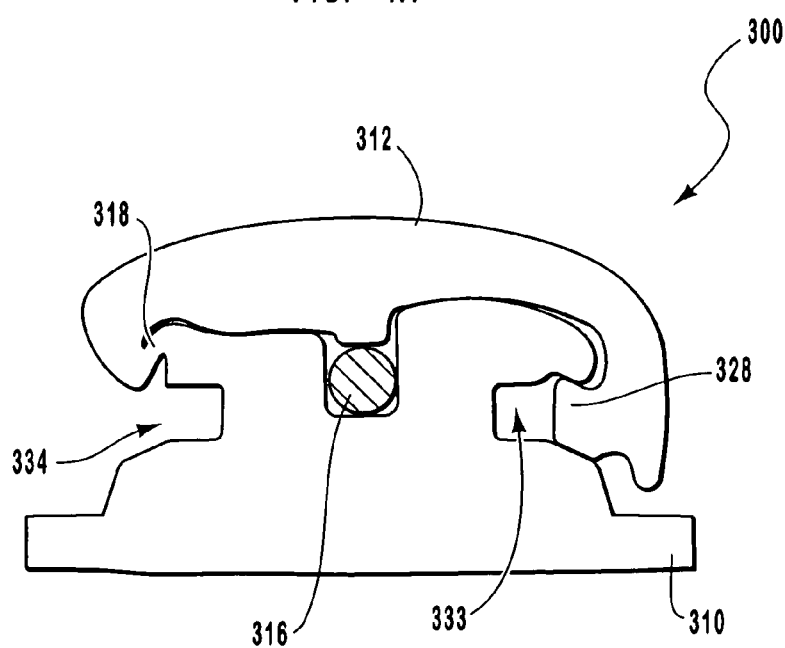

FIGS. 4A and 4B illustrate an alternative bracket embodiment that can also be formed from a crystalline polymer to enhance strength and durability. Bracket 300 is similar to the bracket illustrated in FIGS. 2A-2B in that it includes a bracket base 310, a ligation cover 312, a slot 314, an arch wire 316 (seen in FIG. 4B), an angled keyway 326, a locking tongue 328, and a bearing protrusion 330. This example differs from the bracket illustrated in FIGS. 2A-2B in that although it also uses a film hinge 318 to attach the ligation cover 312 to the bracket base 310, the hinge 318 is not as elongated as hinge 118 shown in FIGS. 2A-2B. Bracket 300 may further include additional arch wire slots 333 and 334 for use with additional or alternative arch wires as known in the art. The crystalline polymer imparts strength and durability to the bracket, which characteristics are especially important to the area surrounding the arch wire slots 314, 333, and 334. According to one embodiment, the crystalline polymer may be blended with an amorphous polymer, so as to lend enhanced elasticity, flexibility, and toughness to the bracket, particularly to the film hinge 318 and the cover 312.

Figure 5A:
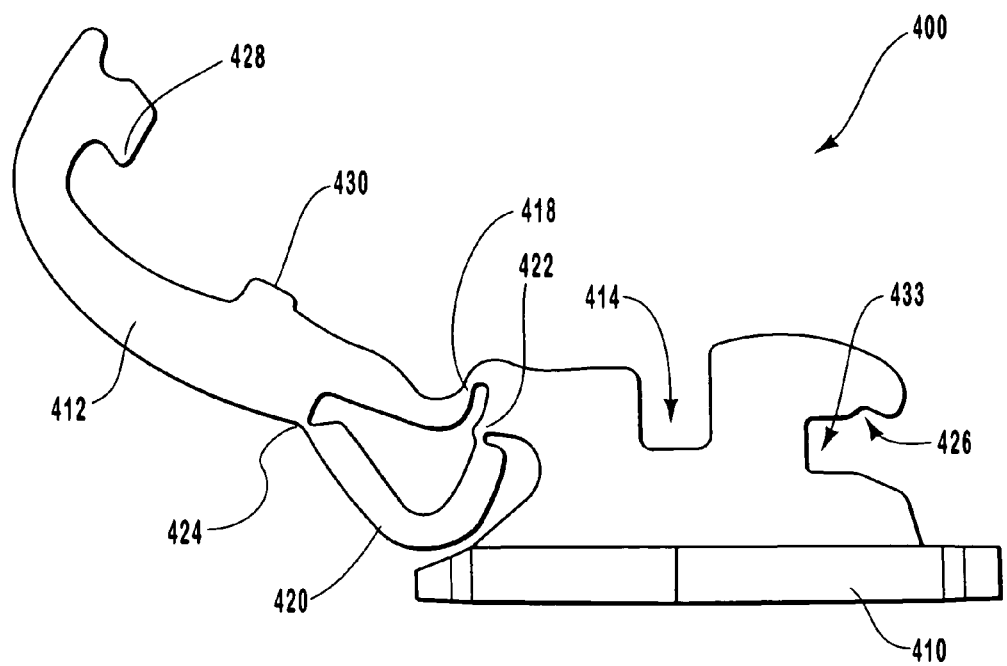
FIGS. 5A-5B illustrate an exemplary self-ligating orthodontic bracket that may comprise a crystalline polymer according to the invention.
Figure 5B:
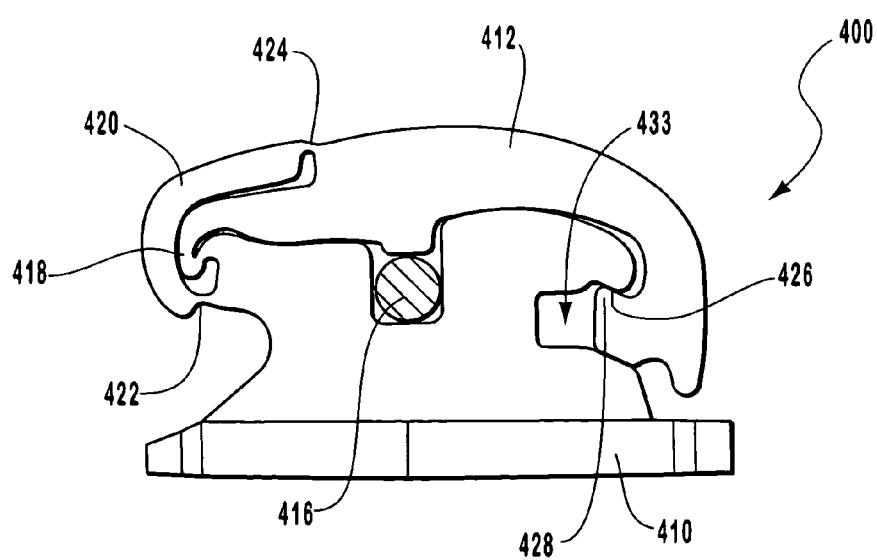

FIGS. 5A and 5B illustrate an alternative bracket embodiment that can also be formed from a crystalline polymer to enhance strength and durability. Bracket 400 includes a bracket base 410, a ligation cover 412, a slot 414, an arch wire 416 (seen in FIG. 5B), a main film hinge 418, an angled keyway 426, a locking tongue 428, a bearing protrusion 430, and an additional arch wire slot 433. This example differs from that illustrated in FIGS. 4A-4B in that it further has a spring element 420 attached at one end of the bracket base 410 by a film hinge 422 and at an opposite end to the ligation cover 412 by a film hinge 424. The crystalline polymer imparts strength and durability to the bracket, which characteristics are especially important to the area surrounding the arch wire slots 414 and 433. According to one embodiment, the crystalline polymer may be blended with an amorphous polymer, so as to lend enhanced elasticity, flexibility, and toughness to the bracket, particularly to the film hinges 418, 422, 424, cover 412, and spring 420.

Figure 6A:
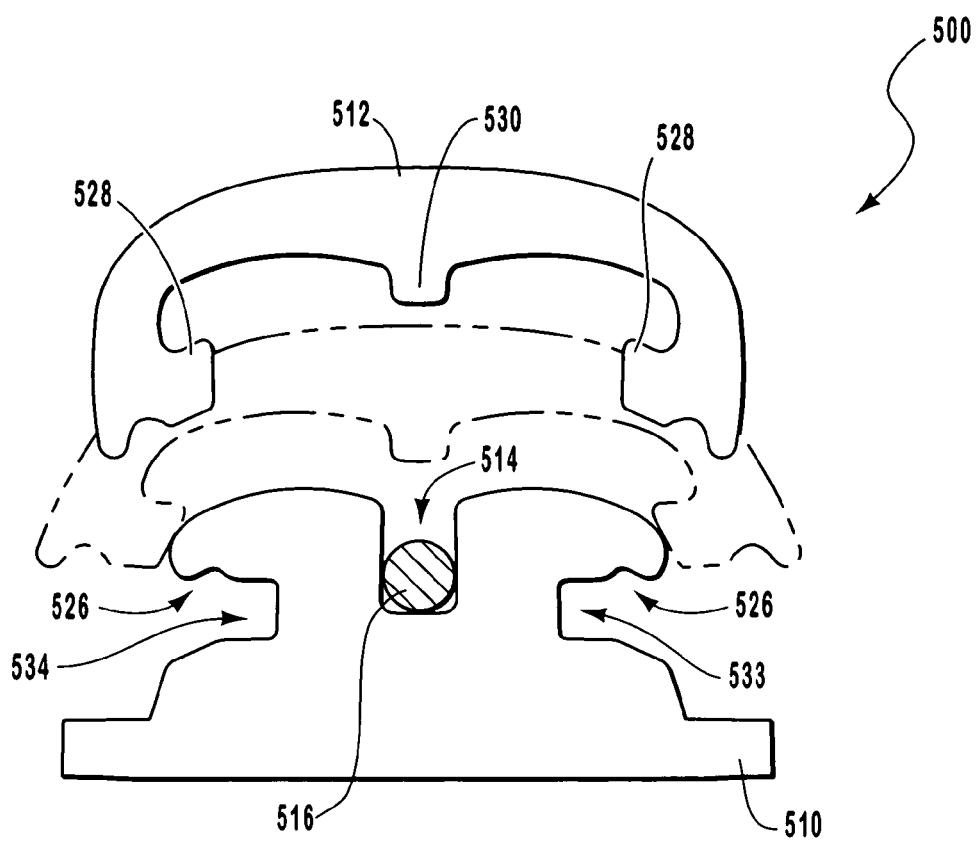
FIGS. 6A-6B illustrate an exemplary self-ligating orthodontic bracket that may comprise a crystalline polymer according to the invention.
Figure 6B:
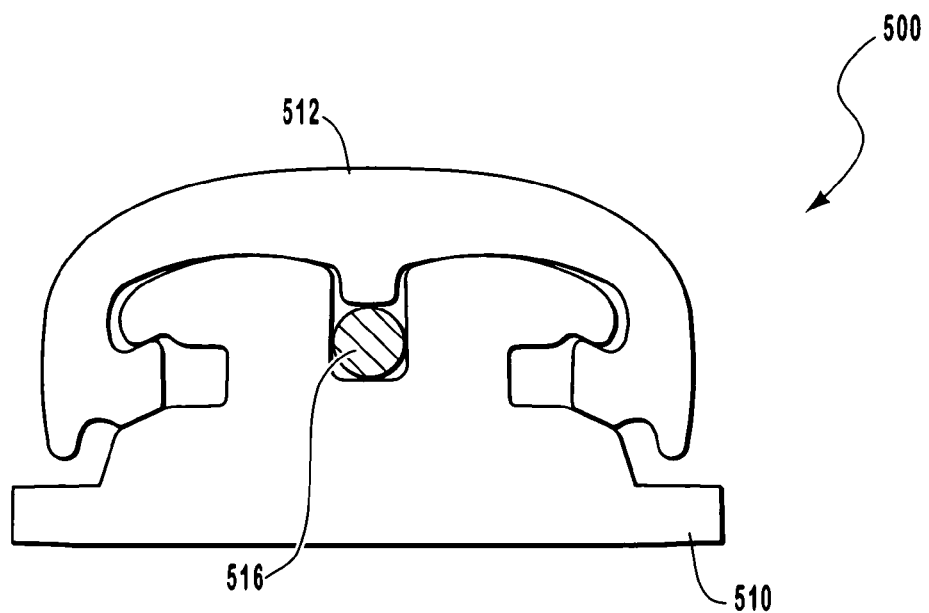

FIGS. 6A and 6B illustrate yet another alternative bracket embodiment that can be formed from a crystalline polymer to enhance strength and durability. Bracket 500 includes a bracket base 510, a ligation cover 512, a slot 514, an arch wire 516, a pair of angled keyways 526, a pair of locking tongues 528, a bearing protrusion 530, and additional arch wire slots 533 and 534. This example differs from that illustrated in FIGS. 2-5 in that it includes no hinge between the base 510 and the cover 512. The bracket base 510 could be used without the cover 512 as a traditional bracket requiring ligatures. Using the cover 512 results in a self-ligating bracket with a uniform, closed, smooth surface across the top surface of the bracket 500, which is beneficial for patient comfort and hygiene.

Various other bracket designs are disclosed in U.S. Pat. No. 6,607,383; U.S. application Ser. No. 09/914,737, filed Aug. 29, 2001, abandoned; and U.S. application Ser. No. 09/953,400, filed Sep. 12, 2001. For purposes of disclosing exemplary orthodontic bracket designs, the foregoing U.S. applications and patent are incorporated by reference.

One exemplary embodiment includes a polymeric blend of both crystalline and amorphous polymers. According to one crystalline/amorphous polymer blend embodiment, a crystalline polymer (e.g., a polyaryletherketone such as PEEK or a crystalline polyamide such as TROGAMID) is included in a range of about 10% to about 90% by weight of the blend, preferably in a range of about 20% to about 80% by weight, more preferably in a range of about 30% to about 70% by weight, and most preferably in a range of about 40% to about 60% by weight. The balance may comprise an amorphous material (e.g. a polyetherimide such as ULTEM) and other components such as fibers, fillers, flow additives, etc.

According to another embodiment, the amorphous material (e.g., a polyetherimide such as ULTEM), is included in a range of about 10% to about 90% by weight of the polymer blend, preferably in a range of about 20% to about 80% by weight, more preferably in a range of about 30% to about 70% by weight, and most preferably in a range of about 40% to about 60% by weight. The balance comprises a crystalline polymer (e.g. a polyaryletherketone such as PEEK or a crystalline polyamide such as TROGAMID) and other components such as fibers, fillers, flow additives, etc.

The following comparative test results illustrate the advantages of forming an orthodontic bracket from crystalline polymers.

EXAMPLE 1

An orthodontic bracket was formed by injection molding several blends of PEEK 151G and ULTEM 1010 polymer resins. The bracket design was the same as that illustrated in FIGS. 2A-2B, which includes a single elongated film hinge with a thickness of about 0.20 mm. With the bracket cover open, the bracket was quite strong and the hinge did not act as a tear line upon which the cover and bracket base separate. In effect, the combination of a more robust bracket design and forming the bracket from a crystalline polymer with an amorphous polymer blended in resulted in a bracket which exhibited enhanced strength and durability, especially when the bracket cover is open. To test the strength and durability of the bracket, specifically the bracket hinge, with the cover closed, the bracket was tested for its loading limit. This was done with a spring balance and appropriate weights. With the bracket cover closed, the bracket exhibited a loading limit of more than 4.0 kg, at which point the cover would separate from the base.

EXAMPLE 2

An orthodontic bracket is formed by injection molding PEEK 151G. The bracket design is the same as that illustrated in FIGS. 2A-2B, which includes a single elongated film hinge with a thickness of about 0.20 mm. Because the bracket is made from a crystalline polymer, it is very strong and resists deformation by an arch wire when used in an orthodontic procedure to straighten teeth. The crystalline polymer is nevertheless sufficiently flexible to allow the elongate film hinge to flex sufficiently while opening and closing the ligation cover.

EXAMPLE 3

An orthodontic bracket is formed by injection molding TROGAMID T grade nylon. The bracket design is the same as that illustrated in FIGS. 2A-2B, which includes a single elongated film hinge with a thickness of about 0.20 mm. Because the bracket is made from a crystalline polymer, it is very strong and resists deformation by an arch wire when used in an orthodontic procedure to straighten teeth. The crystalline polymer is nevertheless sufficiently flexible to allow the elongate film hinge to flex sufficiently while opening and closing the ligation cover.

COMPARATIVE EXAMPLE 1

An orthodontic bracket is formed by injection molding an acetal thermoplastic polymer resin, which is an amorphous resin. The bracket design is the same as that illustrated in FIGS. 2A-2B. Whereas the polymer is sufficiently flexible to allow the cover to open and close repeatedly, over time the bracket experiences deformation due to forces imparted in the arch wire slot by the arch wire during an orthodontic treatment.

COMPARATIVE EXAMPLE 2

An orthodontic bracket is formed by injection molding an amorphous polyamide polymer resin. The bracket design is the same as that illustrated in FIGS. 2A-2B. Whereas the polymer is sufficiently flexible to allow the cover to open and close repeatedly, over time the bracket experiences deformation due to forces imparted in the arch wire slot by the arch wire during an orthodontic treatment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. An orthodontic bracket comprising:
   a bracket base;
   at least one arch wire slot within the bracket base adapted to receive an arch wire therein; and
   a ligation cover that can be selectively moved relative to the bracket base between an open, non-ligating position relative to the arch wire slot and a closed, ligating position relative to the arch wire slot,
   wherein the bracket base and ligation cover comprise at least one type of crystalline polymer,
   wherein the orthodontic bracket has an increased resistance to deformation when an arch wire is positioned within the arch wire slot over time compared to an orthodontic bracket consisting solely of an amorphous polymer.

2. An orthodontic bracket as recited in claim 1, wherein the orthodontic bracket further comprises at least one of fillers, flow additives, glass fibers, carbon fibers, or ceramic fibers.

3. An orthodontic bracket as recited in claim 1, wherein the crystalline polymer comprises a polyaryletherketone.

4. An orthodontic bracket as recited in claim 1, wherein the crystalline polymer comprises a crystalline polyamide.

5. An orthodontic bracket as recited in claim 1, wherein the crystalline polymer is included in an amount in a range of about 10% to about 90% by weight of polymers from which the orthodontic bracket is formed.

6. An orthodontic bracket as recited in claim 1, wherein the crystalline polymer is included in an amount in a range of about 20% to about 80% by weight of polymers from which the orthodontic bracket is formed.

7. An orthodontic bracket as recited in claim 1, wherein the crystalline polymer is included in an amount in a range of about 30% to about 70% by weight of polymers from which the orthodontic bracket is formed.

8. An orthodontic bracket as recited in claim 1, wherein the crystalline polymer is included in an amount in a range of about 40% to about 60% by weight of polymers from which the orthodontic bracket is formed.

9. An orthodontic bracket as recited in claim 1, wherein the bracket base and ligation cover are formed together as a single integral piece.

10. An orthodontic bracket as recited in claim 9, wherein the bracket base and ligation cover are integrally connected together by a flexible integral hinge element.

11. An orthodontic bracket as recited in claim 10, wherein the integral hinge element has increased tensile strength compared to a hinge element consisting solely of an amorphous polymer.

12. An orthodontic bracket as recited in claim 10, wherein the integral hinge element is an elongate film hinge.

13. An orthodontic bracket as recited in claim 1, wherein the bracket base and ligation cover further comprise at least one type of amorphous polymer.

14. An orthodontic bracket as recited in claim 13, wherein the amorphous polymer comprises at least one type of polyetherimide, polycarbonate, or polyaryletherketone.

15. An orthodontic bracket as recited in claim 13, wherein the amorphous polymer is included in an amount in a range of about 10% to about 90% by weight of polymers from which the orthodontic bracket is formed.

16. An orthodontic bracket as recited in claim 13, wherein the amorphous polymer is included in an amount in a range of about 20% to about 80% by weight of polymers from which the orthodontic bracket is formed.

17. An orthodontic bracket as recited in claim 13, wherein the amorphous polymer is included in an amount in a range of about 30% to about 70% by weight of polymers from which the orthodontic bracket is formed.

18. An orthodontic bracket as recited in claim 13, wherein the amorphous polymer is included in an amount in a range of about 40% to about 60% by weight of polymers from which the orthodontic bracket is formed.

19. An orthodontic bracket comprising:
a bracket base;
at least one arch wire slot within the bracket base adapted to receive an arch wire therein; and
a ligation cover integrally attached to the bracket base by a flexible integral hinge element so that the ligation cover can be selectively rotated relative to the bracket base between an open, non-ligating position relative to the arch wire slot and a closed, ligating position relative to the arch wire slot,
wherein the bracket base, ligation cover, and hinge element are integrally formed together as a single piece and compromise at least one type of crystalline polymer and at least one type of amorphous polymer,
wherein the integral hinge element has increased elasticity, flexibility and toughness as compared to a hinge element consisting solely of a crystalline polymer.

20. An orthodontic bracket as recited in claim 19, wherein the crystalline polymer comprises at least one type of polyaryletherketone or crystalline polyamide.

21. An orthodontic bracket comprising:
a bracket base;
at least one arch wire slot within the bracket base adapted to receive an arch wire therein; and
a ligation cover hingedly attached to the bracket base by a flexible elongate film hinge so that the ligation cover is selectively rotatable relative to the bracket base about the elongate film hinge between an open, non-ligating position relative to the arch wire slot in which the arch wire slot is completely unoccluded by the ligation cover and a closed, ligating position relative to the arch wire slot,
wherein the bracket base, ligation cover, and elongate film hinge are integrally formed together as a single piece and comprise at least one type of crystalline polymer,
wherein the orthodontic bracket has an increased resistance to deformation when an arch wire is positioned within the arch wire slot over time compared to an orthodontic bracket consisting solely of an amorphous polymer.

22. An orthodontic bracket comprising:
a bracket base;
at least one arch wire slot within the bracket base adapted to receive an arch wire therein; and
a ligation cover that can be selectively moved relative to the bracket base between an open, non-ligating position relative to the arch wire slot and a closed, ligating position relative to the arch wire slot,
wherein the bracket base and ligation cover are integrally connected together by a flexible integral hinge element,
wherein the bracket base, ligation cover, and hinge element comprise at least one type of crystalline polymer,
wherein the bracket base, ligation cover, and hinge element are formed together as a single integral piece, and
wherein the integral hinge element has increased tensile strength compared to a hinge element consisting solely of an amorphous polymer.

* * * * *

UNITED STATES PATENT AND TRADEMARK OFFICE
CERTIFICATE OF CORRECTION

PATENT NO.        : 7,247,019 B2                                          Page 1 of 1
APPLICATION NO.   : 10/835959
DATED             : July 24, 2007
INVENTOR(S)       : Abels et al.

It is certified that error appears in the above-identified patent and that said Letters Patent is hereby corrected as shown below:

Column 3
Line 3, change "invention;" to --invention.--

Column 10
Line 1, change "compromise" to --comprise--

Signed and Sealed this

Thirteenth Day of November, 2007

JON W. DUDAS
*Director of the United States Patent and Trademark Office*